(12) United States Patent
Sugioka et al.

(10) Patent No.: US 7,302,970 B2
(45) Date of Patent: Dec. 4, 2007

(54) LIQUID DELIVERY DEVICE

(75) Inventors: Hideyuki Sugioka, Palo Alto, CA (US); Takeo Yamazaki, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 262 days.

(21) Appl. No.: 10/526,957

(22) PCT Filed: Sep. 8, 2003

(86) PCT No.: PCT/JP03/11429

§ 371 (c)(1),
(2), (4) Date: Mar. 4, 2005

(87) PCT Pub. No.: WO2004/025128

PCT Pub. Date: Mar. 25, 2004

(65) Prior Publication Data

US 2006/0021651 A1 Feb. 2, 2006

(30) Foreign Application Priority Data

Sep. 10, 2002 (JP) .............................. 2002-264676
Sep. 2, 2003 (JP) .............................. 2003-309901

(51) Int. Cl.
*F16K 11/044* (2006.01)
(52) U.S. Cl. ...................... 137/625.48; 251/11; 251/65
(58) Field of Classification Search ................ 137/113, 137/625.48 I; 251/11 X, 65
See application file for complete search history.

(56) References Cited

U.S. PATENT DOCUMENTS

| | | | |
|---|---|---|---|
| 2,893,416 A | 7/1959 | Hegstad ...................... 137/119 |
| 3,082,748 A | 3/1963 | Vogel .......................... 121/123 |
| 3,112,768 A | 12/1963 | Thompson ................ 137/625.5 |
| 3,256,686 A * | 6/1966 | Lindberg, Jr. ................. 60/516 |
| 3,768,521 A | 10/1973 | Brychta et al. .............. 137/832 |
| 4,114,645 A * | 9/1978 | Pauliukonis ........... 137/625.26 |
| 4,674,526 A * | 6/1987 | Athanassiu .................. 137/113 |

(Continued)

FOREIGN PATENT DOCUMENTS

JP 52-013132 2/1977

(Continued)

OTHER PUBLICATIONS

U.S. Appl. No. 11/030,289, filed Jan. 7, 2005, Takeo Yamazaki et al.

(Continued)

*Primary Examiner*—Stephen M. Hepperle
(74) *Attorney, Agent, or Firm*—Fitzpatrick, Cella, Harper & Scinto

(57) ABSTRACT

A micro liquid delivery device includes a flow channel for flowing a liquid, at least two pressure-generators for generating pressures provided in the flow channel, and a variable member placed between the pressure-generators and capable of transforming between a first stable state and a second stable state by a generated pressure. A branch of the flow channel is selected by transforming the variable member into the first stable state or the second stable state. A valve for changeover of flow channel branches includes a variable member placed between a pressure-generator and transformable between a first stable state and a second stable state by a generated pressure, with the valve serving to select a branch of flow channel branches by the variable member.

5 Claims, 14 Drawing Sheets

U.S. PATENT DOCUMENTS

| | | | |
|---|---|---|---|
| 5,189,991 A * | 3/1993 | Humburg | 137/625.48 |
| 5,671,905 A * | 9/1997 | Hopkins, Jr. | 251/129.01 |
| 6,131,880 A | 10/2000 | Hahn et al. | 251/129.16 |
| 6,283,440 B1 | 9/2001 | Evans | 251/11 |
| 6,494,432 B1 * | 12/2002 | Sticht | 251/11 |
| 6,533,400 B1 | 3/2003 | Kudo et al. | 347/63 |
| 6,828,887 B2 | 12/2004 | Kubby et al. | 335/78 |
| 7,070,699 B2 | 7/2006 | Kubby et al. | 216/24 |
| 2005/0265899 A1 | 12/2005 | Imamura et al. | 422/100 |
| 2006/0054226 A1 | 3/2006 | Yamazaki et al. | 137/827 |

FOREIGN PATENT DOCUMENTS

| | | |
|---|---|---|
| JP | 62-091675 | 4/1987 |
| JP | 5-1669 | 1/1993 |
| JP | 5-240371 | 9/1993 |
| JP | 10/337173 | 12/1998 |
| JP | 2004-025437 | 1/2004 |
| WO | WO 02/33268 | 4/2002 |
| WO | WO 02/40874 | 5/2002 |

OTHER PUBLICATIONS

U.S. Appl. No. 10/480,045, filed Dec. 9, 2003, Takeo Yamazaki et al.

U.S. Appl. No. 10/480,040, filed Dec. 9, 2003, Takeo Yamazaki et al.

U.S. Appl. No. 11/285,069, filed Nov. 23, 2005, Takahiro Ezaki et al.

J.H. Tsai, et al., "A Thermal Bubble Actuated Micro Nozzle-Diffuser Pump", Proceedings of the 14$^{th}$, IEEE International Conference on Micro Electro Mechanical Systems, pp. 409-412 (2001).

J.S. Ko, et al., "Development and Application of a Laterally Driven Electromagnetic Microactuator", Phys. Lett., vol. 81, No. 3, pp. 547-549 (Jul. 15, 2002).

J. Qiu, et al., "A Centrally-Clamped Parallel-Beam Bistable MEMS Mechanism", Proceedings of MEMS, pp. 353-356 (2001).

* cited by examiner 152  151  153

LIQUID DELIVERY DEVICE

TECHNICAL FIELD

The present invention relates to a liquid delivery device. Specifically, the present invention relates to a liquid delivery device which is useful for delivery of a micro quantity of a liquid in chemical analysis apparatuses, medical apparatuses, biotechnology apparatuses, ink-jet printing systems, and the like; particularly to a micro-valve useful for microanalysis systems (μTAS: Micro Total Analysis Systems) for conducting chemical analysis or chemical synthesis on a chip, ink delivery systems of ink-jet printers, and the like systems.

BACKGROUND ART

In recent years with development of three-dimensional fine processing techniques, the systems attracting attention are those which comprise fluid elements such as a fine flow path, a pump, and a valve, and a sensor integrated on a substrate like glass or silicon, and conduct chemical analysis on the substrate. Such a system is called a microanalysis system, a μ-TAS (Micro Total Analysis System), or Lab on a Chip. The miniaturization of the chemical analysis system enables decrease of an ineffective space volume and remarkable decrease of the sample size.

The miniaturization enables also shortening of the analysis time and decrease of power consumption of the entire system. Further, the miniaturization is promising for lowering the price of the system. Furthermore, the μ-TAS is promising in medical services such as home medial care and bed-side monitoring, and biological chemical techniques such as geonomics analysis and proteomics analysis.

Japanese Patent Application Laid-Open No. 10-337173 discloses a micro-reactor for conducting a sequence of biochemical experiment steps comprising mixing solutions to cause reaction, analyzing quantitatively the reaction product, and separating the product, by using combination of cells. FIG. 17 illustrates schematically a concept of micro-reactor 501. Micro-reactor 501 has an isolated reaction chamber closed tightly with a flat plate on a silicon substrate. This micro-reactor has reservoir cell 502, mixing cell 503, reaction cell 504, detection cell 505, and separation cell 506 in combination. By providing such a reactor in plurality on a substrate, many biochemical reactions can be allowed to proceed simultaneously concurrently. Not only the analysis, but material synthesis such as protein synthesis can be conducted in the cells.

Japanese Patent Application Laid-Open No. 5-1669 discloses a valve employing a diaphragm, and a micro-pump utilizing the valve and a piezo element.

U.S. Pat. No. 6,533,400 discloses an ink-jet head employing a valve constituted of a movable member (cantilever).

Jr-Hung Tasai and Liwei Lin: "A Thermal Bubble Actuated Micro Nozzle-Diffuser Pump", Proceedings of the 14th, IEEE International Conference on Micro Electro Mechanical Systems, 2001, pp. 409-412 discloses a valveless micro-pump utilizing a liquid-control function of a bubble generated by heating of the liquid and a nozzle type diffusion element.

Jong Soo Ko, et al.: Appl. Phys. Lett. Vol. 81, No. 3, Jul. 15, 2002, pp. 547-549 discloses an optical switch employing an actuator utilizing interaction of a magnetic field and an electric current.

Jin Qiu, et al.: "Proceedings of MEMS 2001", 2001, pp. 353-356 mentions usefulness of mechanical bistability for relays and valves.

However, conventional micro-valves employing a diaphragm or a cantilever require external force to keep the valve opened or closed as desired.

On the other hand, the mechanically bistable element needs extra driving force for transformation between the two stable structures owing to a high potential energy barrier between the two structures in comparison with an element having no mechanical bistability.

Generally the lower potential energy barrier between the two structures for decreasing the aforementioned extra driving force will make instable the retention of the stable states.

DISCLOSURE OF THE INVENTION

The present invention has been accomplished in view of the aforementioned prior art techniques, and intends to provide a liquid delivery device which is capable of retaining a valve in a closed state or an opened state without applying external force for the retention of the state.

According to an aspect of the present invention, there is provided a liquid delivery device, comprising: a flow channel for flowing a liquid, at least two pressure-generating means for generating pressures provided in the flow channel, and a variable member placed between the pressure-generating means and capable of transforming between a first stable state and a second stable state by a generated pressure; the device serving to select a branch of the flow channel by transforming the variable member into the first stable state or the second stable state.

According to another aspect of the present invention, there is provided a valve for changeover of flow channel branches, comprising a variable member placed between pressure-generating means and transformable between a first stable state and a second stable state by a generated pressure, the valve serving to select a branch of flow channel branches by the variable member.

Thus, the present invention provides a liquid delivery device which is capable of retaining the flow channel in a closed state or an opened state arbitrarily, without applying external force, owing to use of the variable member as flow channel-controlling means for closing or opening the flow channel, the variable member being transformable between the first stable state and the second stable state.

BEST MODE FOR CARRYING OUT THE INVENTION

Preferred embodiments of the present invention are shown below.

The variable member is preferably the liquid delivery device, wherein the variable member is comprised of a flexible resin film, and more preferably comprised of plural flexible resin films linked internally.

The variable member is comprised of an arch-shaped elastic body, and expandable elastic bodies placed on both ends of the arch-shaped elastic body.

The liquid delivery device of the present invention may comprise further a magnetic field-generating means for generating a magnetic field, and the variable member has a means for promoting transformation between the first stable state and the second stable state by the generated magnetic field.

The liquid flow channel is comprised of a first flow channel branch and a second flow channel branch provided with the pressure generating means, and a third flow channel branch is connected to the first flow channel branch and the second flow channel branch, and either the first flow path branch or the second flow channel branch is closed by the variable member.

The liquid delivery device of the present invention preferably comprises further a waste liquid reservoir for receiving a waste liquid from the flow channel, and the waste liquid is introduced into the waste liquid reservoir by selecting the stable state of the variable member. In this case, more preferably, the liquid delivery device comprises further an analysis column for analyzing the liquid, and a pressurizing liquid terminal for introducing the liquid into the analysis column, and the liquid is introduced either into the waste liquid reservoir or into the analysis column by selecting the stable state of the variable member.

In the pressure-generating means of the present invention, the liquid delivery device may be a heater, and the flow channel branch is changed over by growth and contraction of a bubble formed by the heater.

EXAMPLES

Embodiments of the present invention are explained below in more detail by reference to Examples.

First Embodiment

Figure 1:
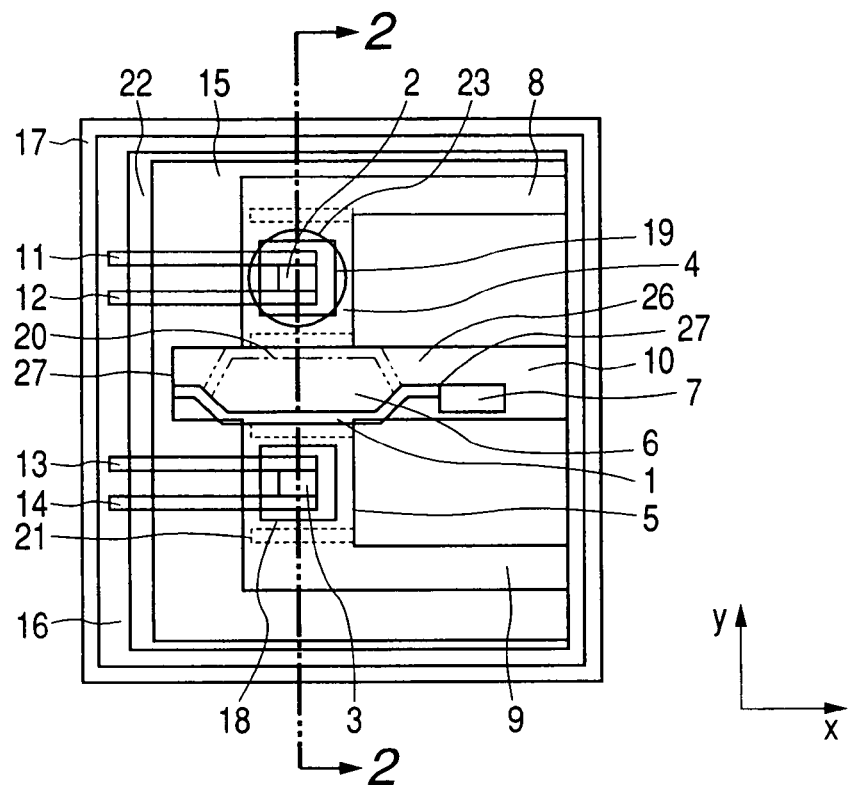
FIG. 1 illustrates schematically a liquid delivery device of a first embodiment of the present invention.

FIG. 1 illustrates a first embodiment of the liquid delivery device of the present invention. Numeral 1 denotes a variable member transformable between a first stable state and a second stable state, the variable member being shown in one stable state in the drawing. The other numerals denote the following: 2 and 3, respectively a heater for bubble formation; 4 and 5, respectively a bubbling chamber; 6, a variable member-retaining chamber; 7, a supporting stand for the variable member; 8 to 10, respectively a flow channel branch; 11 to 14, respectively an electrode; 15, a resin film for comprising the flow channel; 22, an insulating SiN layer of 0.3 μm thick; 16, a heat-reserving $SiO_2$ layer of 2.7 μm thick; 17, an Si substrate of 0.67 mm thick; 18 and 19, respectively a Ta thin film of 0.2 μm thick; 20, the position of the other stable state of variable member 1; 21, an adjusting wall for adjusting the inertance before and after the bubbling chamber and adjusting the inlet aperture size; 23, a bubble generated by heater 2; 27, a supporting portion for variable member 1; and 26, a channel-closing member for opening and closing the flow channel by employing the variable member transformable between the first stable state and the second stable state.

In other words, in this embodiment, a micro-valve as a liquid delivery device is provided which comprises flow channel branches 8-10, variable member 1 transformable between the first stable state and the second stable state, and heaters 2 and 3, and is capable of opening and closing the flow channel by transformation of variable member 1 between the first stable state and the second stable state by utilizing growth or contraction of bubbles generated by the heaters, and is retainable arbitrarily in the closed state or the open state without continuing to add an external force for the retention.

The embodiment may be characterized in that variable member 1 is a flexible resin film in a deflected structure. In this embodiment, the flow channel may be also made of the resin film. In this case, the flow channel and the variable member can be formed effectively in integration by photolithography.

With a simple elastic body, in one method for stabilizing the elastic body equally in the first stable state and the second stable state, a straight flat spring without stress is prepared and deflected. The same level of stability can be obtained by photolithography by utilizing differences in thermal expansion coefficients. However, such a deflected structure at the preparing step, which is referred to as a first stable state in this discussion, is in the most stable state, and a second stable state is a metastable state having a higher energy than the first stable state, being possibly insufficient in the stability. When a resin film having viscoelasticity in a deflected structure is employed as the variable member, such a viscoelastic variable member exhibits an elastic response to an instant external force to retain each of the stable and metastable states, and if any one of the states is held for a relative long time, the member causes a viscous flow so that a shape under the state held is more stable. Accordingly, in this embodiment, a viscoelastic resin film in a flexible structure is preferably employed as the variable member because the metastable state will become stabilized with lapse of time to give a valve of high stability against external disturbance advantageously.

The above-mentioned viscoelastic effects of the resin are made more remarkable preferably by heating the liquid for bubble formation.

The material of the resin film includes cured cation-polymerized epoxy resins; methacrylate ester resins formed from methyl methacrylate, ethyl methacrylate and the like; polymethacrylonitrile; poly-α-methylstyrene; cellulose acetate; polyisobutylene; polymethyl isobutyl ketone; and polymethacrylamide.

This embodiment is characterized also in that a pair of heaters 1 and 2 are respectively placed on each side of variable member 1 and the state of the variable member can be transformed between the first stable state and the second stable state by bubbling caused by the pair of heaters.

The device of this embodiment provides a three-way valve which comprises a first flow channel branch 8, a second flow channel branch 9, and a third flow channel branch 10, and a variable member-holding room 6 containing variable member 1 and connecting the three flow channel branches, a first heater 2 placed in the first channel branch 8, and a second heater 3 placed in the second channel branch 9. Thereby, variable member 1 is transformed by bubbling caused by first heater 2 or second heater 3 between the first stable state and the second stable state to close first channel branch 8 or second channel branch 9. Thus the three-way valve functions (1) to introduce the liquid introduced from third channel branch 10 into first channel branch 8 or second channel branch 9, or (2) to introduce selectively the liquid from first channel branch 8 or the liquid from second channel branch 9 into third channel branch 10.

Figure 2:
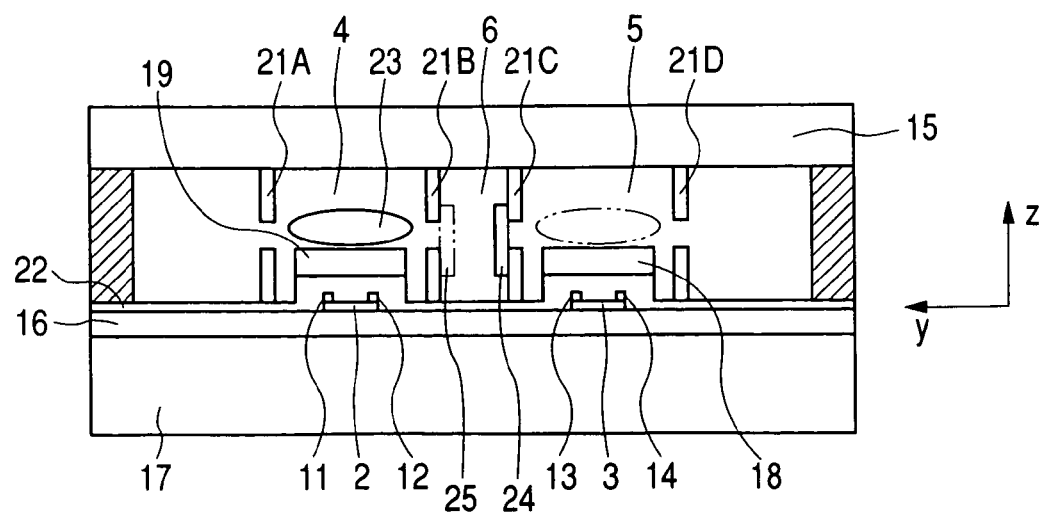
FIG. 2 is a sectional view of the device of the first embodiment of FIG. 1 taken along line 2-2 in FIG. 1.

FIG. 2 is a sectional view of the device of the first embodiment of FIG. 1 taken along line 2-2 in FIG. 1. In FIG. 2, the numerals denote the following: 24, a first stable state of variable member 1; 25, a second stable state of variable member 1; 21A to 21D, respectively an adjusting wall for adjusting the inertance before and after the bubbling chamber and for adjusting the inlet aperture size. Bubbling chambers 4 and 5 and variable member-holding room 6, which also function actually as the flow channel, have respectively a height of 30 µm, and a breadth of 30 µm. Adjusting walls 21A to 21D have respectively a height of 10 µm. The inlet apertures of adjusting walls 21B and 21C have respectively a breadth of 10 µm in the height direction (z direction). Variable member 1 has a breadth of 20 µm in the height direction (z direction). Variable member 1 has a thickness of 5 µm in the y direction. The distance between portions 27 for supporting the variable member is 200 µm.

With such a structure, heating of the liquid by heater 2 brings variable member 1 to a first stable state as shown by numeral 24 in which state the variable member 1 is in contact with adjusting wall 21C for adjusting the size of the inlet aperture.

Figure 3:
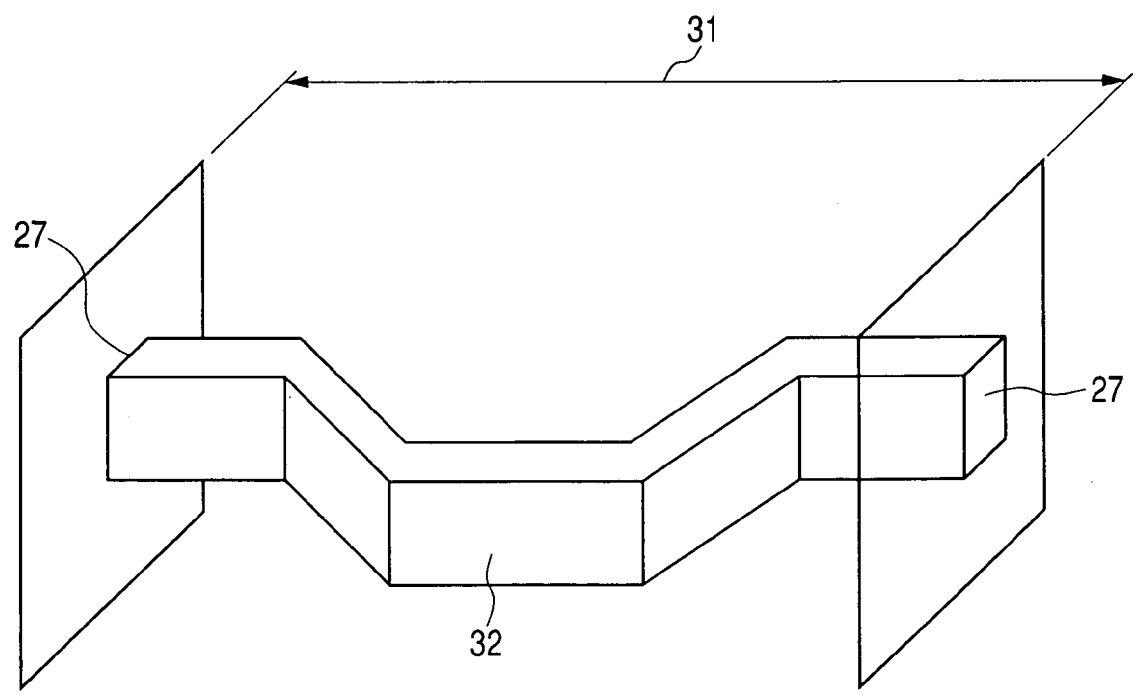
FIG. 3 illustrates schematically a steric structure of variable member 1 having a deflected structure of an embodiment of the liquid delivery device of the present invention.

FIG. 3 illustrates schematically a steric structure of variable member 1 having a deflected structure of this embodiment. In FIG. 3, deflectable portion 32 longer than the distance 31 between supporting portions 27 for the variable member is kept at a first stable state or a second stable state at the positions nearly symmetrical as shown by numerals 1 and 20 in FIG. 1 with respect to the line connecting the supporting portions 27.

Figure 4A:
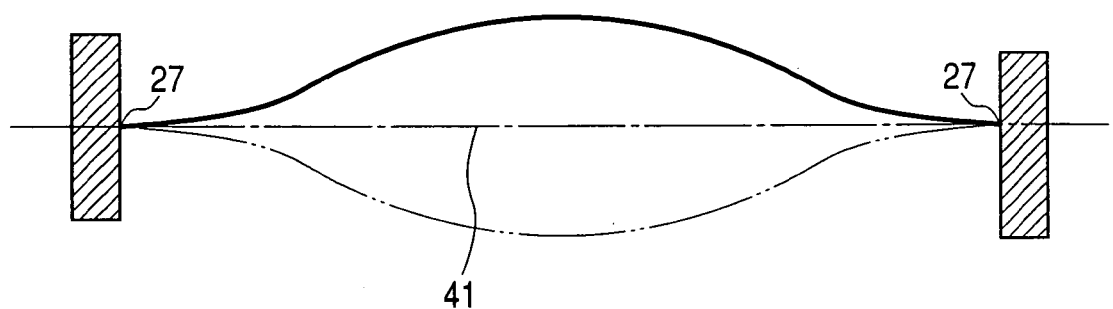
FIGS. 4A and 4B illustrate schematically variable member 1 in a gently deflected structure.
Figure 4B:
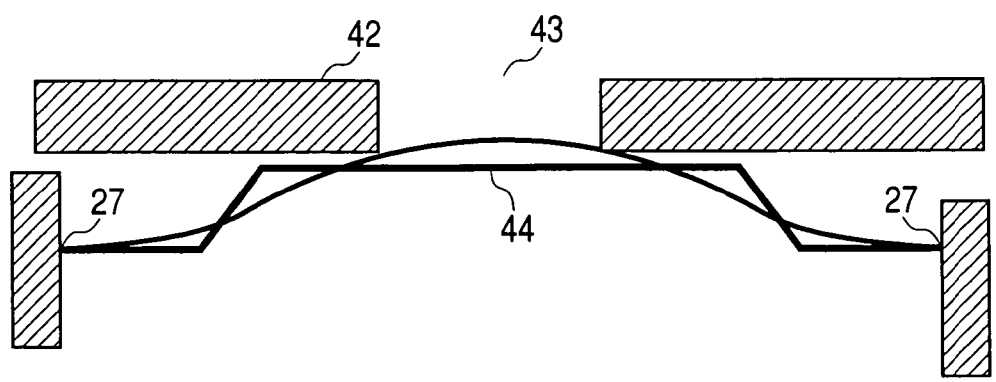

FIGS. 4A and 4B illustrate schematically the variable member in a gently deflected structure. This deflection structure may be formed with gentle deflection so as to be supported by supporting portions 27 on both sides with respect to the center line 41 as shown in FIG. 4A. In this case also, a stable state can be obtained, when the variable member is pressed against wall 42 having inlet aperture 43, to close the flow channel with complicated deformation of the variable member as shown in FIG. 4B. Such a closing state is also shown schematically with simplification as shown by numeral 44.

Figure 5A:
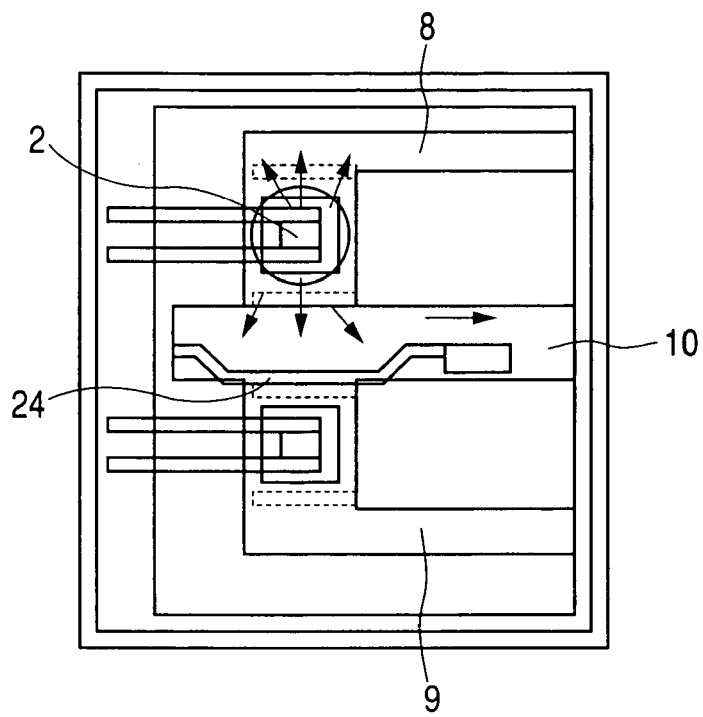
FIGS. 5A and 5B illustrate schematically basic function of the first embodiment of the liquid delivery device of the present invention.
Figure 5B:
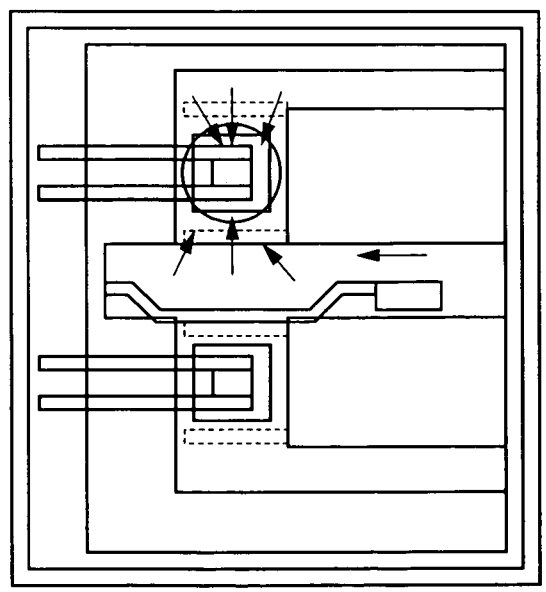

FIGS. 5A and 5B illustrate schematically a basic operation of the first embodiment of the liquid delivery device of the present invention. FIGS. 5A and 5B shows operation of a micro-valve of this embodiment in which a liquid is allowed to bubble by heating by application of voltage to heating resistor 2. In FIG. 5A, variable member 1 in a first stable state is transformed into second stable state 24 by bubble formation at a high pressure of about 100 atm and bubble growth to cross a potential barrier to the variable member transformation to open first flow channel branch 8 and close second flow channel branch 9. FIG. 5B shows the state of bubble contraction. In FIG. 5B, variable member 1 in the second stable state 24 tends to return to the first stable state owing to the contraction of the bubble. However, variable member 1 is retained in the second stable state, since there is a potential barrier corresponding to the stabilization energy for transformation of the variable member to be crossed between the first stable state and the second stable state and the pressure difference in the contraction is about 1 atm or less, much smaller than the pressure difference of bubbling.

In this embodiment, third channel branch 10 is formed in a direction parallel to variable member 1, whereby the variable member is less affected by the flow during contraction of the bubble, advantageously.

Figure 6A:
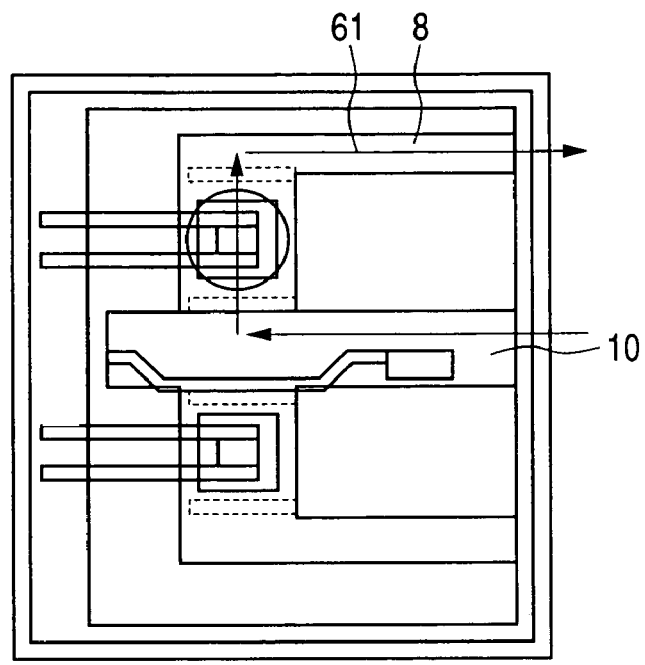
FIGS. 6A and 6B illustrate schematically the function of selecting the flow channel branches in the first embodiment of the liquid delivery device of the present invention.
Figure 6B:
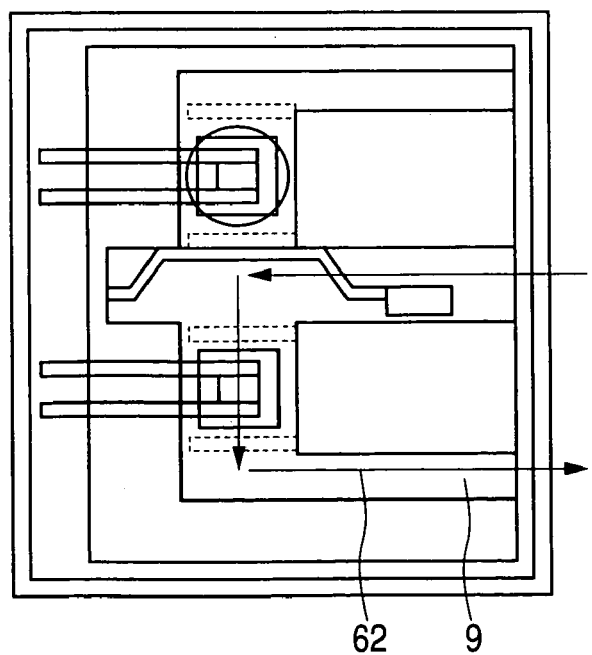

FIGS. 6A and 6B illustrate schematically the function of changing over the flow channel branches in the first embodiment of the present invention. FIGS. 6A and 6B shows the function of changeover of the flow channel branches realized by a micro-valve of this embodiment. FIG. 6A shows flow route 61 of the liquid introduced through third channel branch 10 and fed to first flow channel branch 8. FIG. 6B shows flow route 62 of liquid introduced through third channel branch 10 and fed to second channel branch 9. Otherwise, the reverse flow direction of routes 61 and 62 can be utilized as a two-input/one-output type of liquid changeover element.

In this embodiment, heating resistors 2 and 3 are thin TaN films of 0.05 µm thick, and the heating body has a size of 25 µm×25 µm and has a resistance of 53 Ω. The variable member is transformed by a rectangular pulse of 8 V, 1 µs between the stable states.

Second Embodiment

Figure 7:
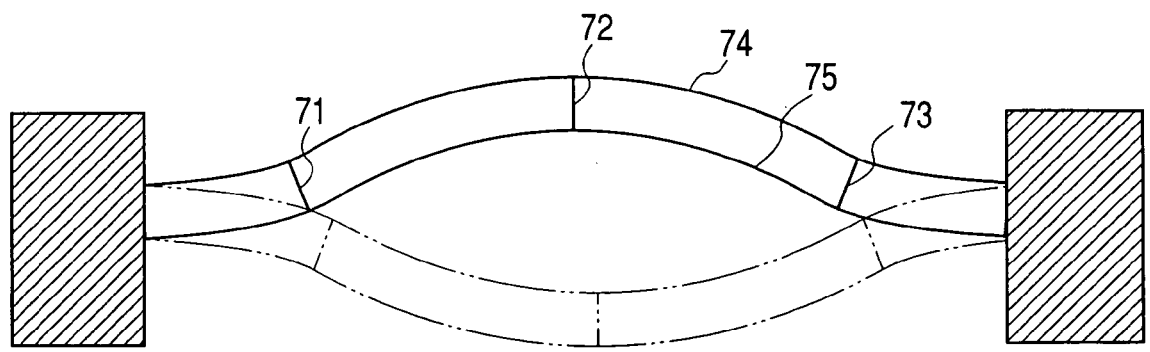
FIG. 7 illustrates schematically a second embodiment of the liquid delivery device of the present invention.

FIG. 7 illustrates schematically a second embodiment of the liquid delivery device of the present invention. FIG. 7 shows the feature of the second embodiment. This embodiment is nearly the same as the first embodiment except that the variable member is constituted of plural deflectable resin films 74 and 75 linked by linking films 71, 72 73.

The variable member constructed of viscoelastic resin films linked by linking films can realize a stable valve for tight closure.

The material for the resin film includes cured cation-polymerized epoxy resins; methacrylate ester resins formed from methyl methacrylate, ethyl methacrylate and the like; polymethacrylonitrile; poly-α-methylstyrene; cellulose acetate; polyisobutylene; polymethyl isobutyl ketone; and polymethacrylamide.

Third Embodiment

Figure 8:
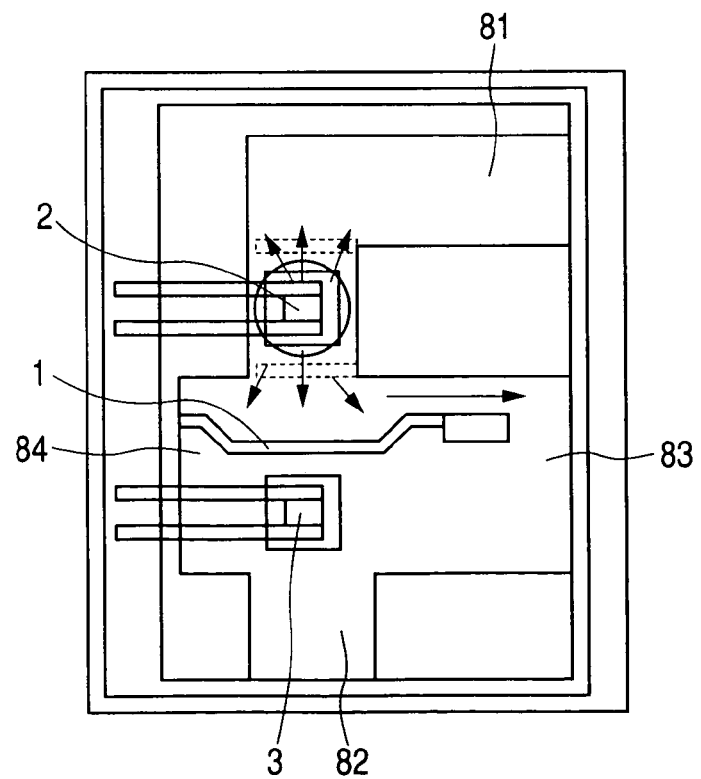
FIG. 8 illustrates schematically a third embodiment of the liquid delivery device of the present invention.

FIG. 8 illustrates schematically a third embodiment of the liquid delivery device of the present invention. FIG. 8 shows the feature of the third embodiment. This embodiment is nearly the same as the first embodiment except that the device comprises first flow channel branch 81, second flow channel branch 82, third flow channel branch 83, variable member-holding room 84 which holds the variable member 1 and connects the above three flow channel branches together, and a pair of heaters 2 and 3 placed on each side of the variable member; and the first flow branch is closed and opened with the variable member by bubbling caused by the pair of heaters.

Figure 9A:
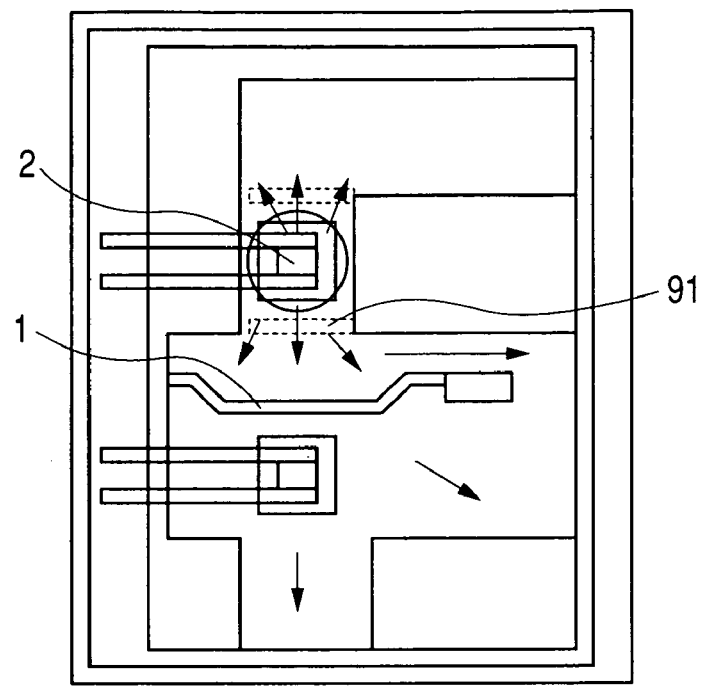
FIGS. 9A and 9B illustrate schematically a first basic function of the third embodiment of the liquid delivery device of the present invention.
Figure 9B:
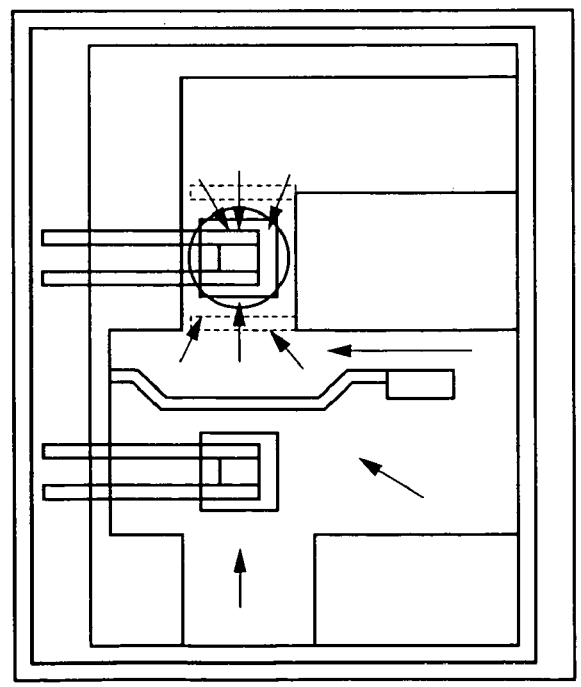
Figure 10A:
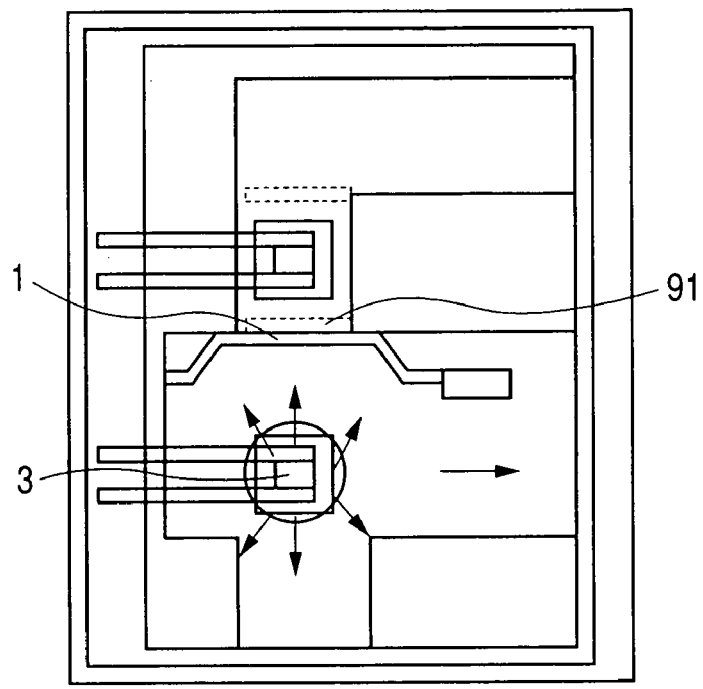
FIGS. 10A and 10B illustrate schematically a second basic function of the third embodiment of the liquid delivery device of the present invention.
Figure 10B:
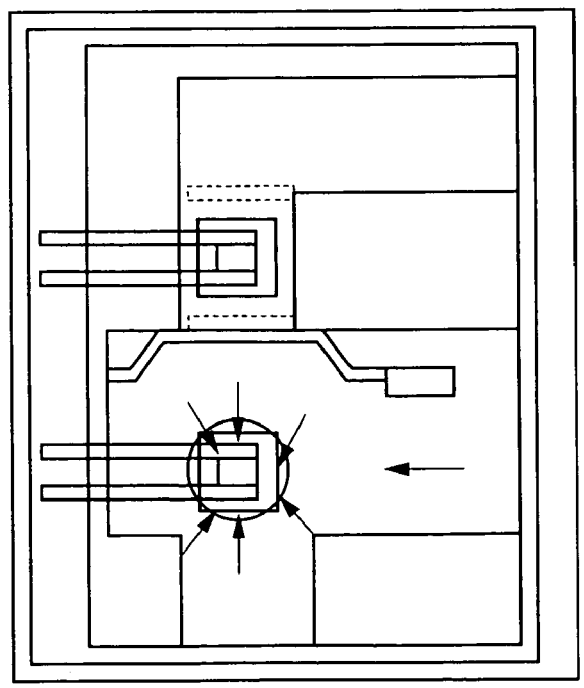

In this embodiment, bubbling caused by heater 2 brings variable member 1 into the second stable state to open inlet 91 as shown in FIGS. 9A and 9B, whereas bubbling caused by heater 3 brings variable member 1 into the first stable state to close inlet 91 as shown in FIGS. 10A and 10B.

Figure 11A:
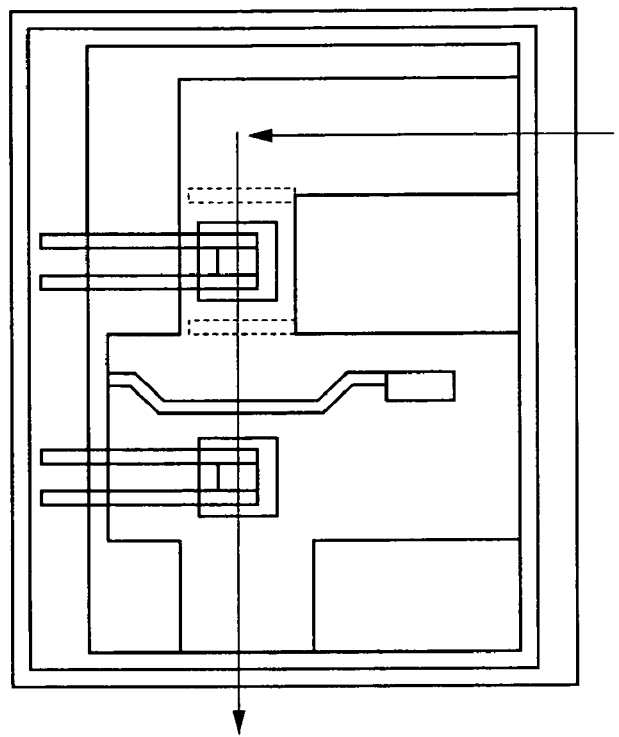
FIGS. 11A and 11B illustrate schematically the function of switching the flow channel branches in the third embodiment of the liquid delivery device of the present invention.
Figure 11B:
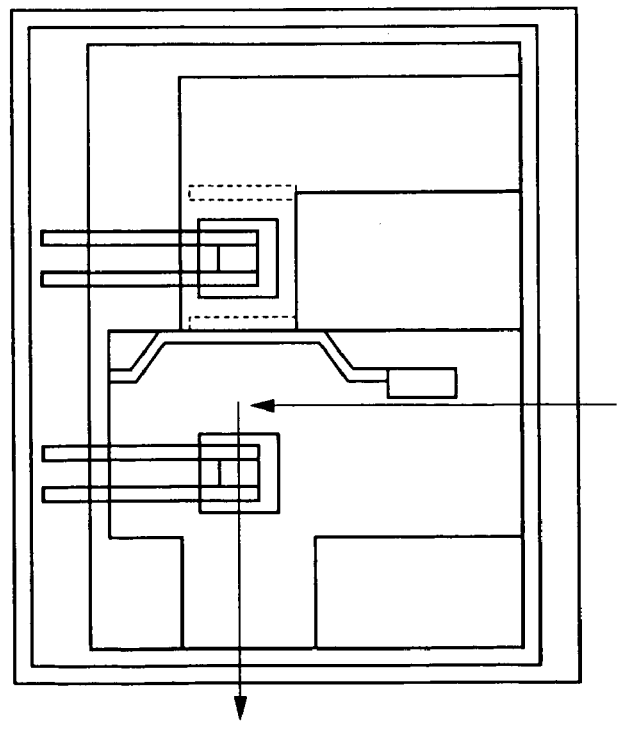

The valve of this embodiment opens and closes selectively only a specific one of the three flow channel branches as shown in FIGS. 11A and 11B.

Fourth Embodiment

Figure 12:
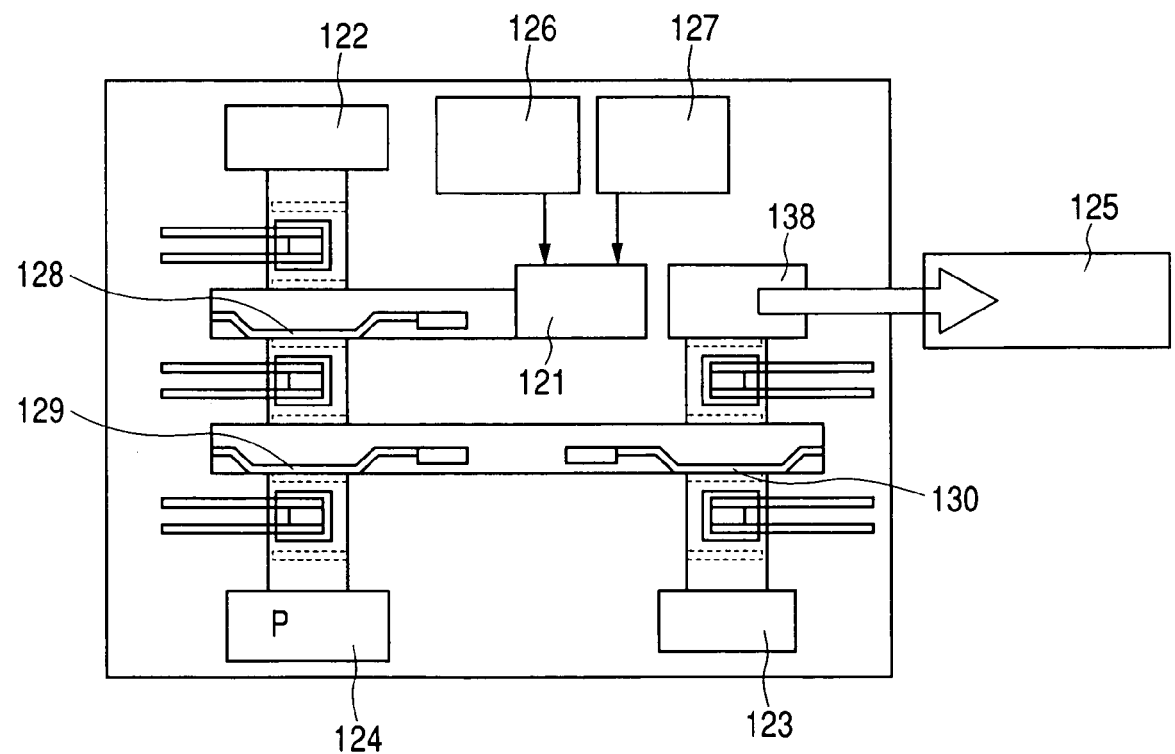
FIG. 12 illustrates schematically a fourth embodiment of the liquid delivery device of the present invention.

FIG. 12 illustrates schematically a fourth embodiment of the liquid delivery device of the present invention. This embodiment, as shown in FIG. 12, is nearly the same as the first embodiment and the third embodiment except that the device comprises sample room 121, first waste liquid reservoir 122, second waste liquid reservoir 123, pressurizing liquid terminal 124, analysis column connecting terminal 138, a flow channel, and variable members 128, 129 and 130; and routes (a), (b) and (c) below are formed by changeover of the variable member:

(a) a route for flow of the liquid from the sample room to the first waste liquid reservoir,
(b) a route for flow of the liquid from the sample room to the second waste liquid reservoir, and
(c) a route for flow of the liquid from the sample room to the analysis column-connecting terminal.

Here the "waste liquid" includes a liquid having been used for washing of the flow channel, and like liquids. That is, the waste liquid having used for flow channel washing is sent to the waste liquid reservoir. In this example, two waste liquid reservoirs are provided, but the reservoir is not limited thereto.

In FIG. 12, numeral 126 denotes a sample room, for example, for promoting initiation of production of protein, and numeral 127 denotes a sample room for storing a solution for dissolving the protein. A solution containing a protein to be analyzed is sent out from sample room 121 to the analysis column 125 for the analysis.

The terminal for pressurization is used for introducing a liquid into the analysis column. The liquid is introduced into the analysis column by application of a pressure.

Fifth Embodiment

Figure 13:
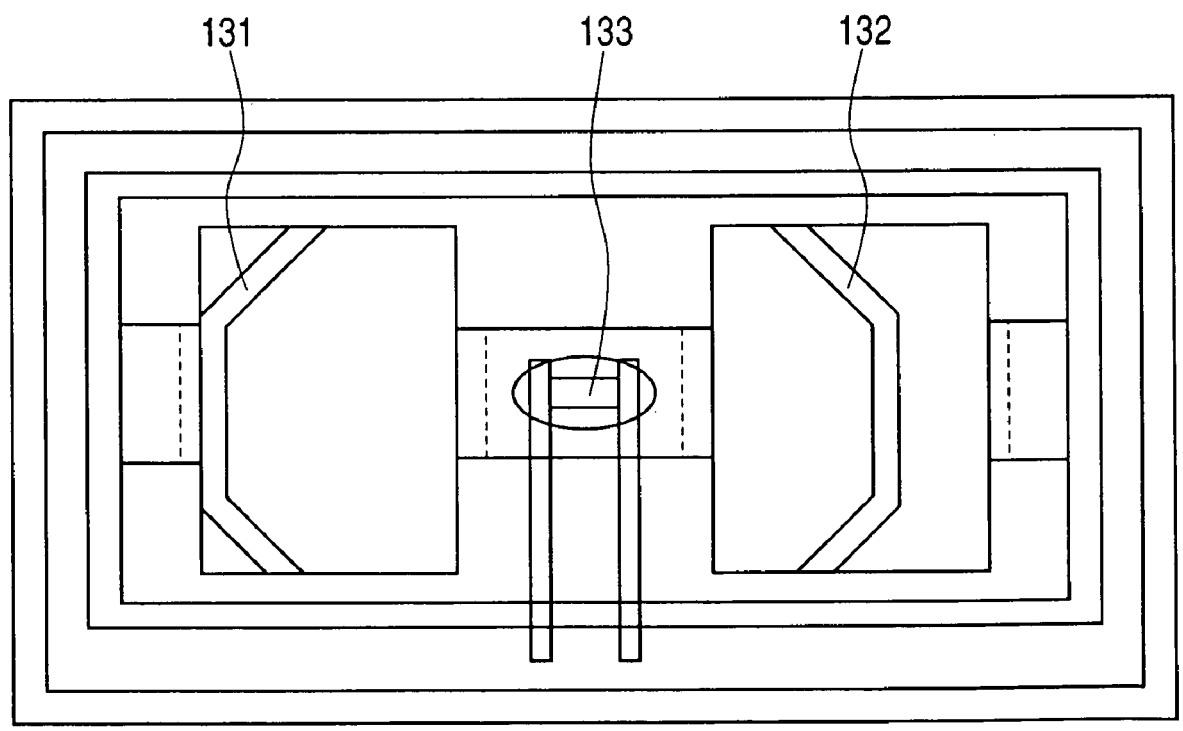
FIG. 13 illustrates schematically a fifth embodiment of the liquid delivery device of the present invention.

FIG. 13 illustrates schematically a fifth embodiment of the liquid delivery device of the present invention. This embodiment, as shown in FIG. 13, is nearly the same as the first embodiment and the third embodiment except that the device has a flow channel, a pair of variable members 131 and 132 having respectively a first stable state and a second stable state, and a heater 133 between the pair of variable members for bubble formation, one variable member 131 functions to prevent a back flow to allow the liquid flow toward the heater only, and the other variable member 132 functions to prevent a back flow to allow the flow from the heater only.

Figure 14A:
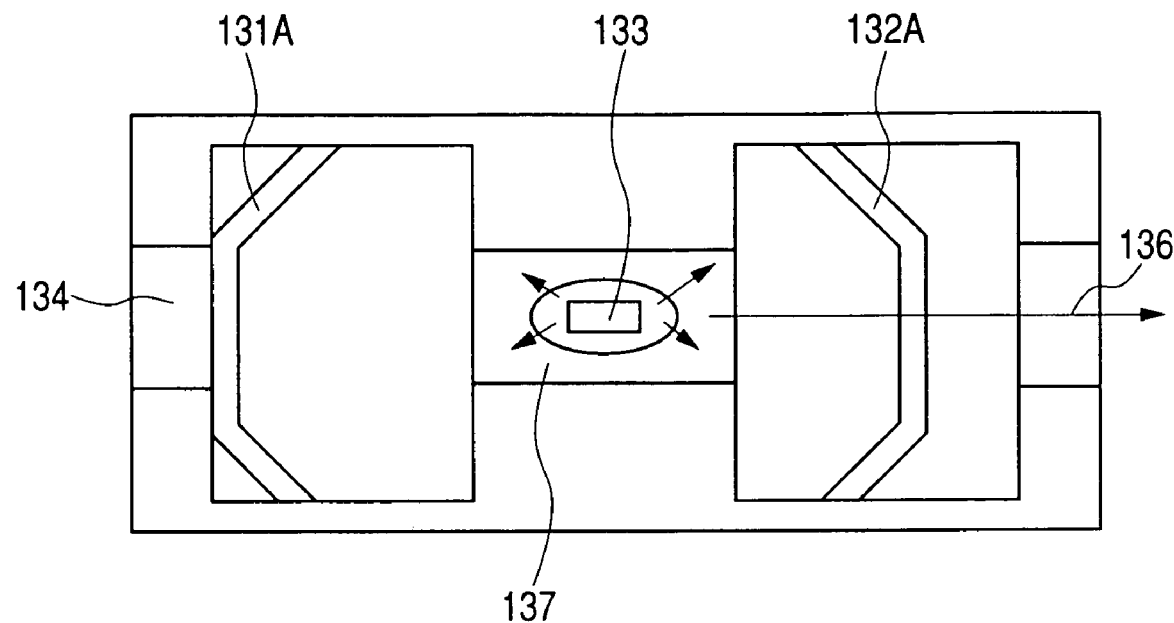
FIGS. 14A and 14B illustrate schematically the function of switching the flow channel in the fifth embodiment of the liquid delivery device of the present invention.
Figure 14B:
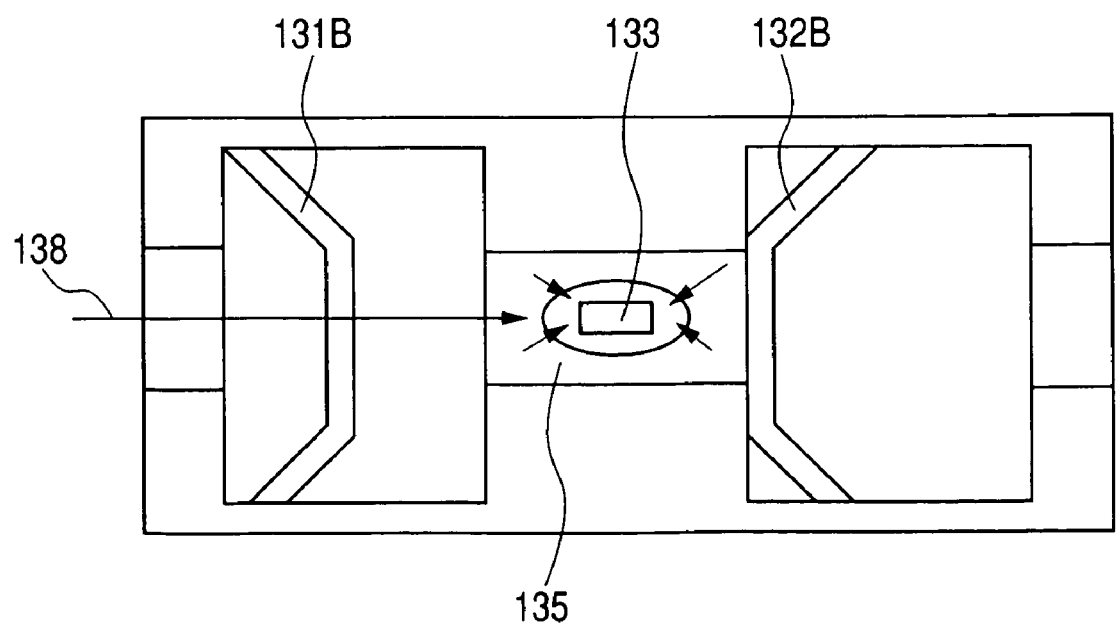

FIGS. 14A and 14B show the basic operation in the fifth embodiment of the liquid delivery device of the present invention. In this embodiment, as shown in FIGS. 14A and 14B, the growing bubble brings variable member 131 into a stable state 131A to close the liquid inlet 134, and variable member 132 into a stable state 132A to open the liquid inlet 135. Thereby the liquid in bubbling chamber 137 is delivered in the direction 136.

The contraction of the bubble brings variable member 131 into a stable state 131B to open liquid inlet 134, and variable member 132 into a stable state of 132B to close liquid inlet 135. Thereby the liquid is introduced in direction 138 into bubbling chamber 137.

As described above the micro-valve of the second embodiment functions as a pump mechanism by utilizing the two flows 136 and 138.

Sixth Embodiment

Figure 15:
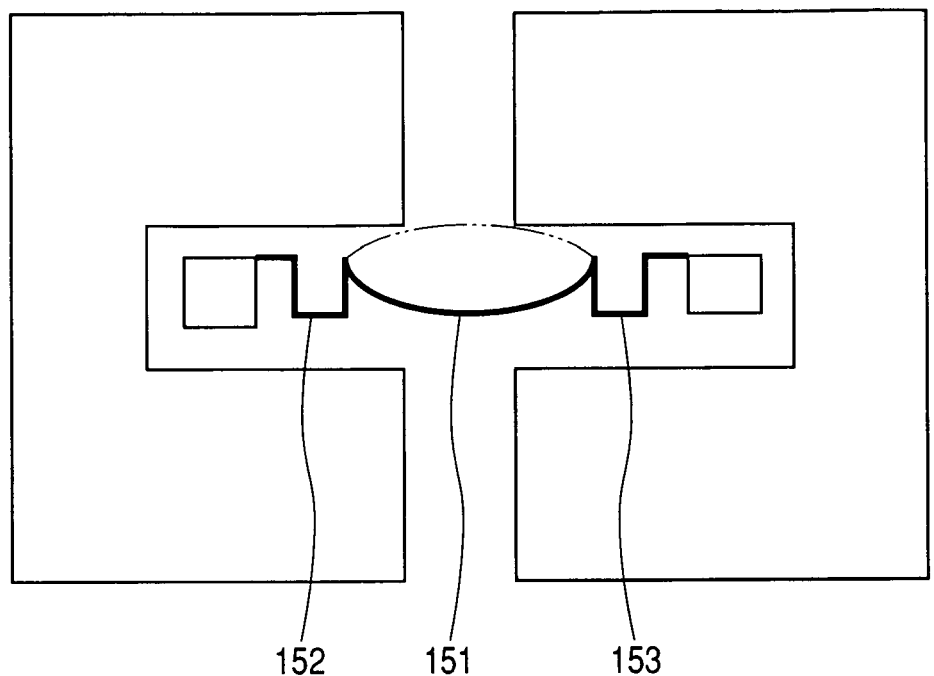
FIG. 15 illustrates schematically a sixth embodiment of the liquid delivery device of the present invention.

FIG. 15 illustrates schematically a sixth embodiment of the liquid delivery device of the present invention. This embodiment, as shown in FIG. 15, is nearly the same as the first embodiment and the third embodiment except that the variable member is comprised of arch-shaped spring 151 and a pair of expansion springs 152, 153 on each side of the arch-shaped spring.

In this embodiment, the pair of expansion springs 152, 153 enables effective adjustment of the stability and the potential barrier.

Seventh Embodiment

Figure 16:
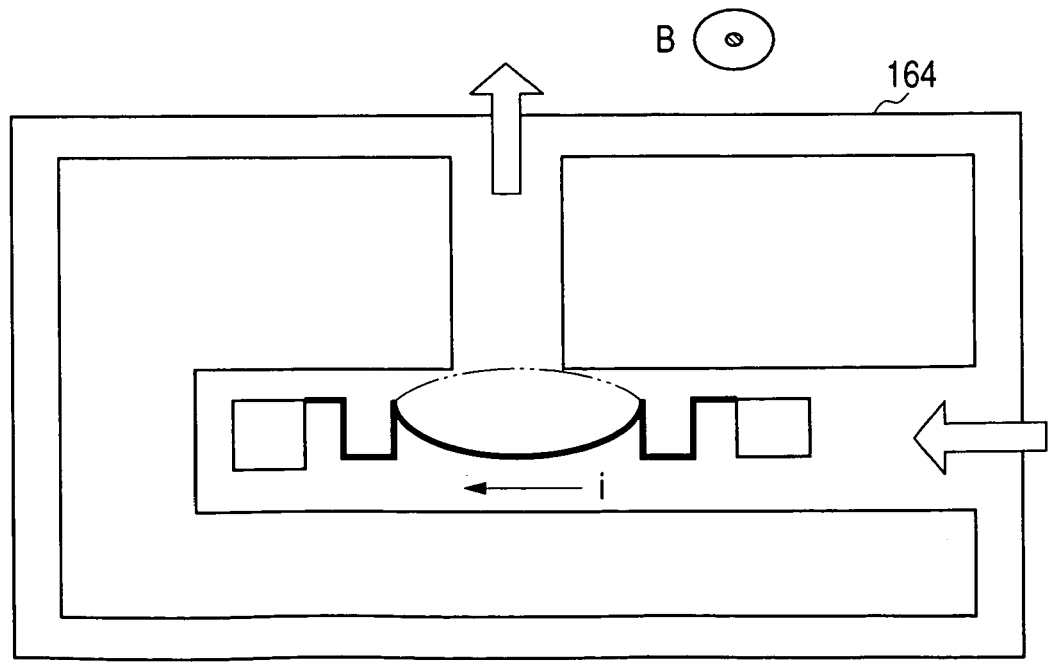
FIG. 16 illustrates schematically a seventh embodiment of the liquid delivery device of the present invention.
Figure 17:
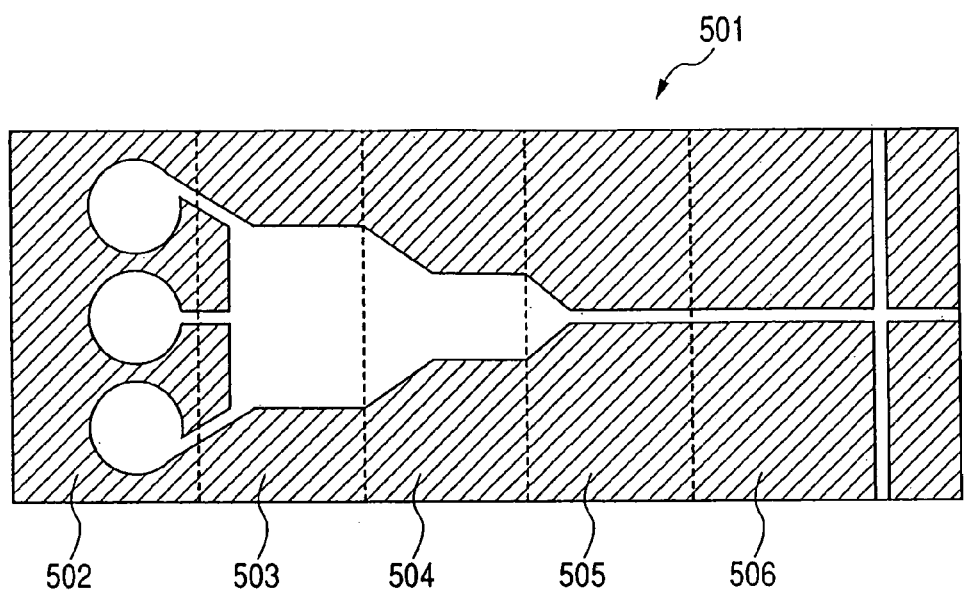
FIG. 17 illustrates schematically a conventional microreactor.

FIG. 16 illustrates schematically a seventh embodiment of the liquid delivery device of the present invention. This embodiment, as shown in FIG. 16, is nearly the same as the first embodiment and the third embodiment except that the device has an electroconductive variable member and a magnetic field-generating means for generating magnetic field B, and an electric current flow i promotes the transformation between the first stable state and the second stable state.

In FIG. 16, the magnetic field is generated by a plate-shaped permanent magnet 164 composed of NdFeB with a magnetic flux density of 3000 G. On the bubble formation, application of electric current of about 700 mA to the variable member strengthen the force of the bubble by Lorentz force to drive the variable member toward the first stable state or the second stable state.

The liquid delivery device of this invention is useful as a micro-valve for a micro total analysis system (μTAS) for conducting chemical analysis or chemical synthesis on a chip, and an ink feeding system in an ink-jet printer.

Eighth Embodiment

Figure 18:
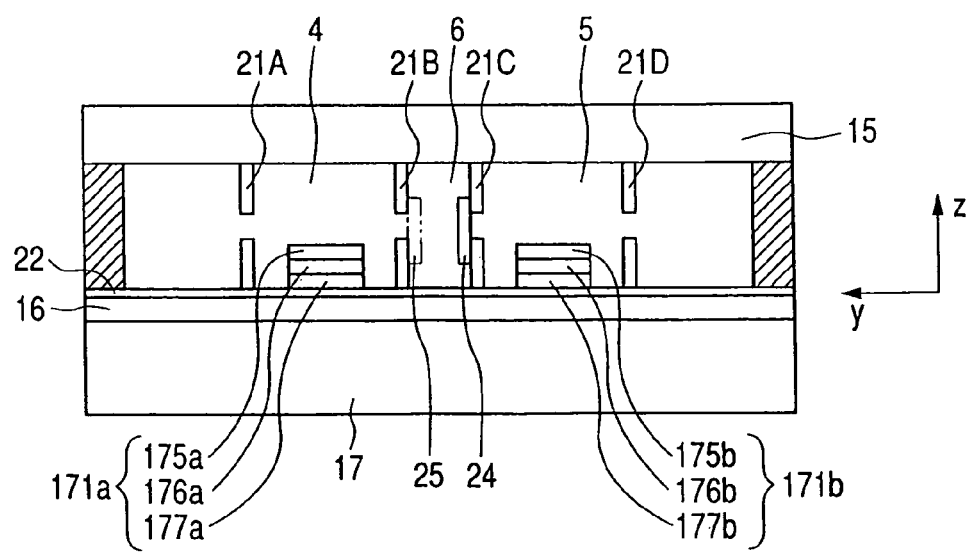
FIG. 18 illustrates schematically an eighth embodiment of the liquid delivery device of the present invention.

FIG. 18 shows features of an eighth embodiment. The numerals denote the following: 175a, 175b, 177a, and 177b, respectively an electrode for applying a voltage to a piezo element; 176a and 176b, respectively a piezoelectric material layer; 171a and 171b, respectively a piezoelectric element as the pressure-generating means.

This embodiment is the same as First Embodiment except that piezoelectric elements are used as the pressure-generating means.

The invention claimed is:

1. A micro liquid delivery device, comprising:
   a flow channel for flowing a liquid,
   first and second pressure-generating means for generating pressures provided in the flow channel, and
   a variable member placed between the first and second pressure-generating means and having bistability capable of transforming between a first stable state and a second stable state by a generated pressure, wherein the variable member is comprised of a flexible resin film and is transformed into the first stable state or the second stable state to select a branch of the flow channel.

2. The liquid delivery device according to claim 1, wherein the variable member is comprised of a plurality of flexible resin films linked internally.

3. A micro liquid delivery device, comprising:
   a flow channel for flowing a liquid,
   first and second pressure-generating means for generating pressure provided in the flow channel, and
   a variable member placed between the first and second pressure-generating means and having bistability capable of transforming between a first stable state and a second stable state by a generated pressure, wherein the variable member comprises an arch-shaped elastic body and is transformed into the first stable state or the second stable state to select a branch of the flow channel.

4. A micro liquid delivery device, comprising:
   a flow channel for flowing a liquid,
   first and second pressure-generating means for generating pressures provided in the flow channel,
   a variable member placed between the first and second pressure-generating means and having bistability capable of transforming between a first stable state and a second stable state by a generated pressure, wherein the variable member is transformed into the first stable state or the second stable state to select a branch of the flow channel, and
   a magnetic field-generating means for generating a magnetic field, wherein
   the variable member includes means for promoting transformation between the first stable state and the second stable state by the generated magnetic field.

5. A micro liquid delivery device, comprising:
   a flow channel for flowing a liquid,
   first and second pressure-generating means for generating pressures provided in the flow channel, and
   a variable member placed between the first and second pressure-generating means and having bistability capable of transforming between a first stable state and a second stable state by a generated pressure, wherein the variable member is transformed into the first stable state or the second stable state to select a branch of the flow channel,
   a waste liquid reservoir for receiving a waste liquid from the flow channel, and the waste liquid is introduced into the waste liquid reservoir by selecting the stable state of the variable member,
   an analysis column for analyzing the liquid, and
   a pressurizing liquid terminal for introducing the liquid into the analysis column, and the liquid is introduced either into the waste liquid reservoir or into the analysis column by selecting the stable state of the variable member.

* * * * *